United States Patent [19]
Graf et al.

[11] Patent Number: 5,584,417
[45] Date of Patent: *Dec. 17, 1996

[54] DISPENSER FOR DISCHARGING A FLUID MEDIUM

[75] Inventors: Lothar Graf, Rielasingen-Worblingen; Karl-Heinz Fuchs, Radolfzell, both of Germany

[73] Assignee: Ing. Erich Pfeiffer GmbH & Co. KG, Germany

[*] Notice: The term of this patent shall not extend beyond the expiration date of Pat. No. 5,469,989.

[21] Appl. No.: 546,428

[22] Filed: Oct. 20, 1995

Related U.S. Application Data

[62] Division of Ser. No. 320,794, Oct. 7, 1994, Pat. No. 5,469,989, which is a continuation of Ser. No. 958,367, filed as PCT/EP91/01181, Jun. 25, 1991, abandoned.

[30] Foreign Application Priority Data

Jul. 4, 1990 [DE] Germany ............... 40 21 263.7

[51] Int. Cl.$^6$ .................................... B67D 5/00
[52] U.S. Cl. .................. 222/82; 222/135; 222/327
[58] Field of Search ............... 222/82, 83.5, 309, 222/325, 327, 135, 386, 321.7

[56] References Cited

U.S. PATENT DOCUMENTS

| | | |
|---|---|---|
| 2,810,473 | 10/1957 | Oden et al. . |
| 3,132,772 | 5/1964 | Bristow . |
| 3,796,348 | 3/1974 | Zipper . |
| 3,802,608 | 4/1974 | Gullett . |
| 4,015,717 | 4/1977 | Richardson et al. . |
| 4,131,217 | 12/1978 | Sandegren ............... 222/82 |
| 4,308,977 | 1/1982 | Sigmund et al. . |
| 4,445,626 | 5/1984 | Steffen et al. ............ 222/309 X |
| 4,456,152 | 6/1984 | Young et al. . |
| 4,627,432 | 12/1986 | Newell et al. . |
| 4,946,069 | 8/1990 | Fuchs . |
| 4,962,868 | 10/1990 | Borchard . |
| 4,994,029 | 2/1991 | Rohrbough ............. 222/82 X |
| 5,307,953 | 5/1994 | Regan . |
| 5,469,989 | 11/1995 | Graf et al. ............ 222/82 |

FOREIGN PATENT DOCUMENTS

| | | |
|---|---|---|
| 090659 | 10/1983 | European Pat. Off. . |
| 2561912 | 10/1985 | France . |
| 2583463 | 12/1986 | France . |
| 2625981 | 7/1989 | France . |
| 2917281 | 11/1979 | Germany . |
| 3541378 | 5/1986 | Germany . |
| 3734306 | 4/1989 | Germany . |
| 3909632 | 9/1990 | Germany . |
| 587166 | 4/1977 | Switzerland . |
| 998765 | 7/1965 | United Kingdom . |
| 2197693 | 5/1988 | United Kingdom . |

Primary Examiner—Gregory L. Huson
Attorney, Agent, or Firm—Quarles & Brady

[57] ABSTRACT

A dispenser is disclosed which is made up of two telescoping sections. One section holds at least one volume of a substance to be discharged. Telescoping motion of the sections compresses the substance to be discharged to force it through a passage in the section not holding the substance volume to be discharged therefrom. Motion between the section is limited to ensure precise metering of a charge to be dispersed.

14 Claims, 2 Drawing Sheets

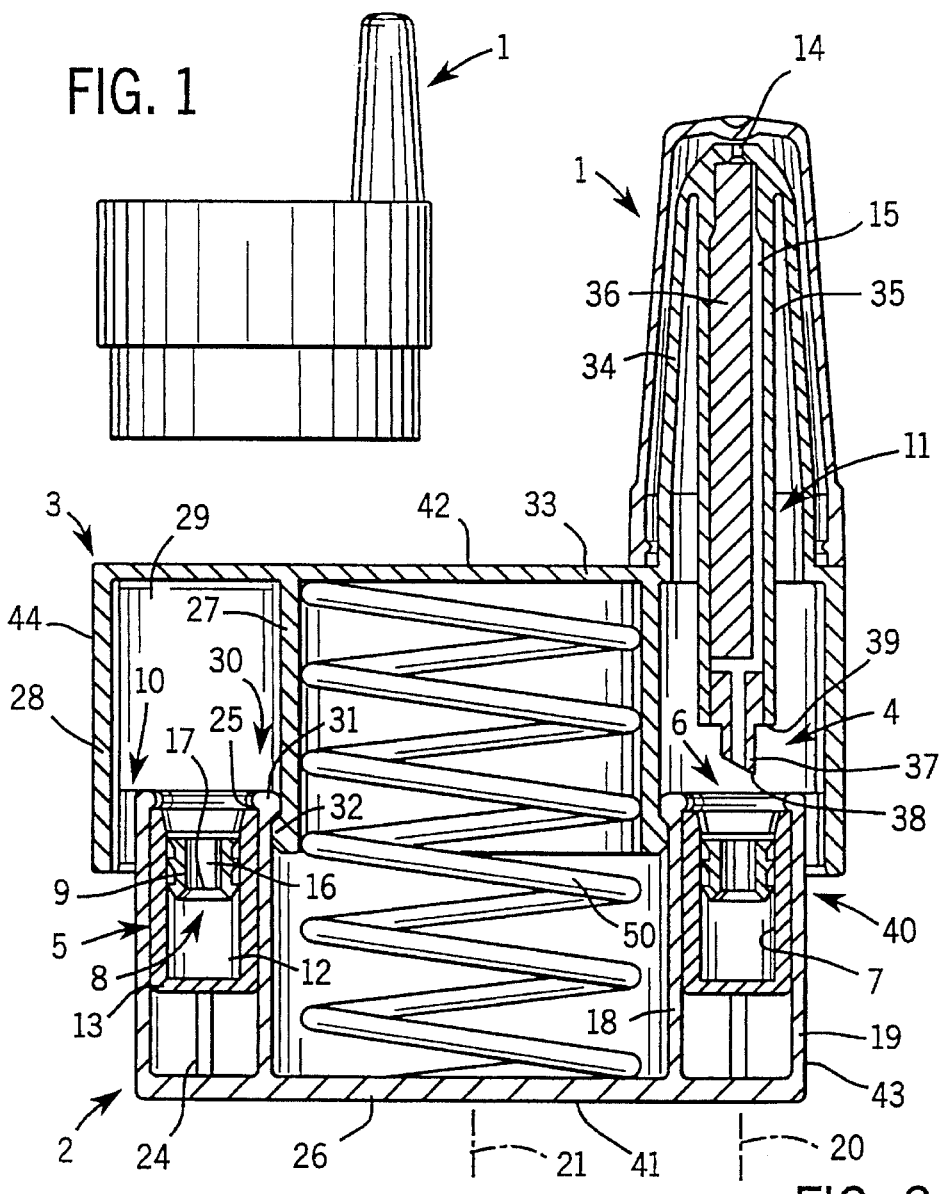
FIG. 1
FIG. 2
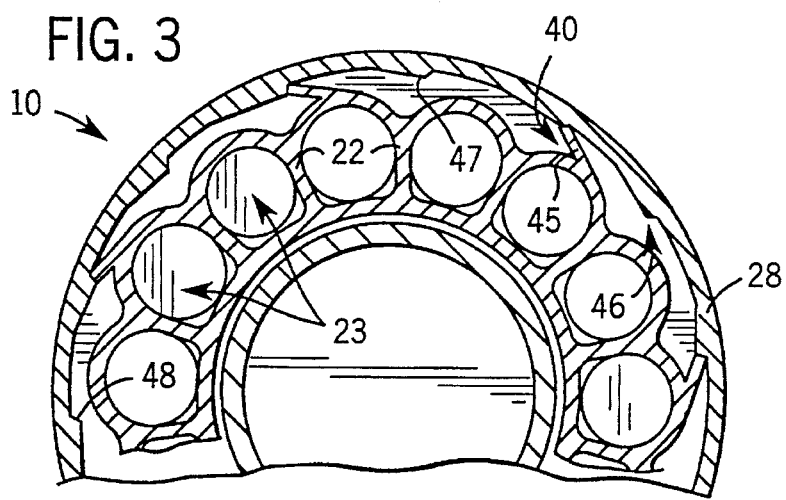
FIG. 3

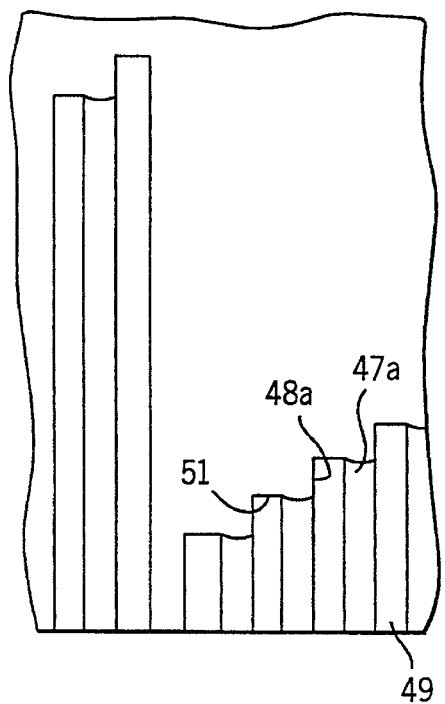
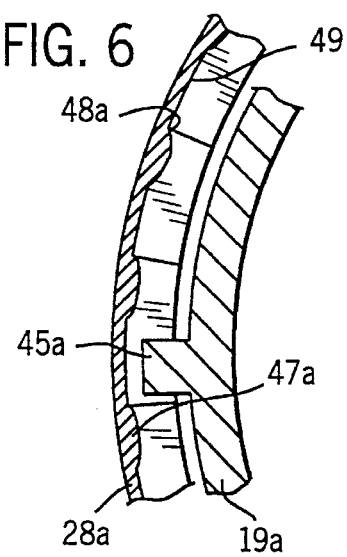
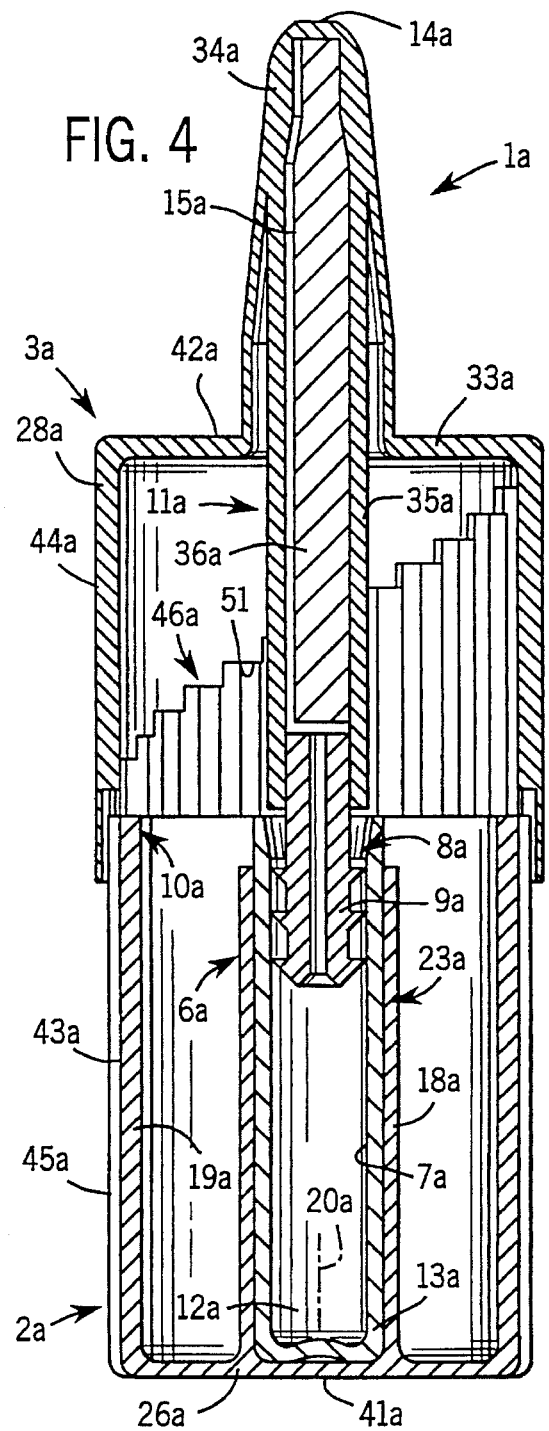
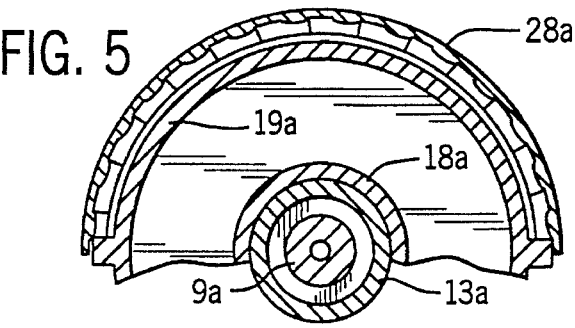

DISPENSER FOR DISCHARGING A FLUID MEDIUM

This is a division of application Ser. No. 08/320,794 filed Oct. 7, 1994, and now U.S. Pat. No. 5,469,989, which is a continuation of application Ser. No. 07/958,367, filed as PCT/EP91/0118, Jun. 25, 1991, now abandoned.

BACKGROUND OF THE INVENTION

The invention relates to a discharge apparatus for flowable media, which can be in the pulverulent, gaseous and/or pasty, but in particular in the liquid state, and which are mainly used for cosmetic or pharmaceutical purposes.

The application of such media in individual, successive, material or volume-identical or different charges or batches can be appropriate. For this purpose it is admittedly advantageous to equip the discharge apparatuses with meters or counters for the discharged batch quantities, but this leads to a relatively complicated and space-consuming construction. It is also possible with conventional pump dosing devices to successively discharge batches of the same or of different sizes, if an adjustable dosing mechanism is provided. However, in this case the number of the already discharged batches or charges cannot be established.

SUMMARY OF THE INVENTION

In accordance with the invention it is desired to avoid the problems and disadvantages of known constructions, and in particular provide a discharge apparatus with which it is possible to successively discharge in simple manner discharge batches, optionally in precisely predetermined order. Appropriately, the discharge apparatus is constructed for discharge by a manual stroke or operating movement.

In addition, the discharge apparatus can appropriately be switched from the starting position for one operating stroke to the starting position for the next operating stroke independently of the size of the discharge volume through the particular operating stroke. In the case of a non-curved, but instead substantially linear operating stroke, the pump can be transferred stepwise in its stroke direction between the individual starting positions, e.g., in such a way that the stroke end position of one operating stroke is the starting position for the next operating stroke. Instead of this or in addition thereto, the switching over can also take place transversely to the stroke direction, so that successive discharges take place from different pump chambers.

The construction according to the invention is particularly suitable for the discharge of a plurality, e.g., seven, fourteen or more discharge batches, such as is necessary if, e.g., one active substance is to be used once a day for one, two or more weeks.

Despite this relatively large number of switching steps, the discharge apparatus can be given a very compact construction. In the case of the object of the invention at the end of each preceding discharge cycle there can be an automatically engaging and operating locking of the following discharge cycle by the sequence control. The latter must be manually actuated in order to release said following discharge cycle and only then is the locking means overcome and can the following discharge cycle take place. This makes it possible to fix a specific sequence of discharge batches or charges, because namely the sequence control so fixes the succession of two or more batches, that between the latter there is a blocking of the discharge possibility, which can only be overcome again by a separate release actuation.

Appropriately, the discharge apparatus has as the discharge unit at least one thrust piston pump or one or more, substantially dimensionally stable pump cylinders or medium reservoirs and indestructible storage capsules for the medium, so that the pump cylinder can e.g., be made from glass and very high hygienic requirements are satisfied. This is further improved if the filled discharge apparatus contains the medium only in at least one container such that it simultaneously forms the pump cylinder for guiding a pump piston and facing same in a spaced manner in the starting position, is tightly sealed at the bottom, namely does not have an intake or suction opening.

In order that the discharge apparatus can always only be indexed in the correct direction, a locking mechanism or ratchet locking against the opposite direction is provided and can be constructed in the manner of a freewheel.

In the case of the described or some other construction of the discharge apparatus, it is advantageous if at least part of the plunger of a piston unit is substantially separated in one starting position from the piston unit and can only be coupled by a pivoting and/or stroke movement with the pump piston. If the pump piston is already located within the pump cylinder, it can form a tight closure for the medium stored in the pump chamber. On coupling the plunger the closure is automatically opened, e.g., by destruction and simultaneously produces a line connection between the pump chamber and an outlet channel or an outlet opening. As the medium can be stored in completely sealed manner in the pump chamber with such a construction, very long storage times can be obtained. In addition, the coupling process can be such that it forms a safety mechanism against unauthorized use, e.g., by children.

The discharge apparatus can be a very simple construction. For example it has two substantially one-piece, telescopically interengaging caps, whose remote, exposed end walls directly form pressure handles for stroke operation, whereas its exposed outer circumferences form gripping handles for turning operation used for indexing purposes. Appropriately, a discharge connecting piece carrying the plunger projects over one of these end walls, while the other end wall forms the associated end limitation of the discharge apparatus. At least one receptacle for the plug-in fastening of a storage or cylinder container is provided in the interior of the associated cap completely concealed with respect to the outside.

It is particularly advantageous if a plurality of storage or cylinder containers are arranged in a row or a circular ring in such a way that with the said sequence control one container after the other can be emptied, particularly through the same discharge opening.

Thus, substantially for each discharge a new, sealed container is broken open, which only has to have a storage volume of, e.g., approximately 0.1 ml. Such a discharge apparatus can be very small dimensions of e.g. approximately a diameter of 5 cm and, without discharge connecting piece, has a smaller axial extension.

BRIEF DESCRIPTION OF THE DRAWINGS

These and further features of preferred developments of the invention can be gathered from the claims, the description and the drawings and the individual features, both singly and in the form of subcombinations, can be realized in an embodiment of the invention and in other fields and can represent advantageous, independently protectable constructions for which protection is hereby claimed. Embodiments of the invention are described in greater detail hereinafter relative to the drawings, wherein:

FIG. 1 is an elevation view of a discharge apparatus according to the invention shown roughly in actual size.

FIG. 2 is an axial section view of the discharge apparatus shown on a larger scale.

FIG. 3 shows a cross-section through the arrangement according to FIG. 2.

FIG. 4 shows another construction in axial section.

FIG. 5 shows a cross-section through FIG. 4.

FIG. 6 is a detailed view of FIG. 5 on a larger scale.

FIG. 7 is an elevation view of the inner circumference of the cap according to FIG. 4 in developed detail.

DETAILED DISCUSSION

The discharge apparatus 1 is bounded on its outside substantially by two casing bodies 2 and 3, which interengage in the manner of a flat box with lid and internally receive a pump arrangement 4 with a plurality of pumps 6 so as to be completely concealed from the outside.

With each pump 6 is associated a cylinder 7 of a cylinder arrangement 5, which forms with a pump piston 9 of a piston unit 8 a standard subassembly. With a sequence control 10 each pump can be transferred from an inoperative position into an operative position, in which it is roughly equiaxially oriented with a plunger 11 for operating purposes and its pump chamber 12 formed by a container 13 can be directly emptied into the open by means of an outlet channel 15 through an outlet opening 14.

To this end, each pump 6 has in an equiaxial passage opening 16 of its sleeve-like pump piston 9, a closure 17, e.g., in the form of a very thin diaphragm, whose edge is tightly fixed to the inner face of the passage opening 16. In the starting position the pump piston 9 is located entirely within the container 13 adjacent to its end open to the full inside diameter of the cylinder 7 and forms with the closure 17 a plug tightly sealing the pump chamber 12 to the outside. The pump piston 9, e.g., has three axially succeeding sealing lips constructed in one piece with the piston sleeve and which are used exclusively for the retaining thereof and the guidance thereof on the cylinder track.

The base and jacket of each container 13 are constructed in one piece and the closure 17 is located at the end of the pump piston 9 or the passage opening 16 facing the base. All the pumps 5 are arranged in approximately axially parallel manner to one another, to the plunger 11 and to the particular casing body 2 or 3 in such a way that their ends are in each case roughly in a common plane.

The substantially cylindrical base or casing body 2 having a smaller external diameter has two approximately coaxially interengaging jackets 18 and 19, which are connected in one piece with one another by means of roughly radial webs 22 and form between in each case two webs a mounting support 23 for a pump 5 or a container 13. The axes 20 of the mounting supports 23 are positioned in a ring about the common axis 21 of the casing, from which the central axis of the plunger 11 has the same spacing. On the bottom of each mounting support 23, which forms an axial plug-in opening closely adapted to the container 13, is provided a support 24, e.g., at least one rib, on which is supported the associated container 13 with its base spaced from the bottom of the plug-in opening.

The open face of the container 13 is overlapped by a toroidal notch 25 of the retaining jacket, which gives a clearance-free snap fastening of the container 13, which extends approximately up to the open, inner face of the casing body 2. At the outer face the casing body 2 is closed by an approximately planar end wall 26. In the starting position the casing body 2 projects out of the casing body 3 over most of its length. The casing body 3 has two coaxially interengaging jackets 27 and 28, between which is defined an annular space 29 for the rotary and axially displaceable engagement of the circular retaining projection of the casing body 2.

The guide 30 is essentially only formed by the inner jackets 18 and 27, a bead 31 on the inner end of the jacket 18 slides on the inner circumference of the jacket 27 and a bead 32 on the inner end of the jacket 27 slides on the inner circumference of the jacket 18. The beads 31 and 32 simultaneously form snap members for a simple assembly connection of the casing bodies 2 and 3 and the sole axial securing means for fixing the starting position, in which they engage with one another by ring shoulders. The jackets 27 and 28 are also constructed in one piece with a substantially planar end wall 33, which with the end wall 26 forms the end boundaries of the casing and over which only projects a connecting piece 34 receiving the plunger 11 in flush manner and having the outlet opening 14 in its end face.

An outer connecting piece jacket is connected in one piece to the end wall 33 and at its free end passes into an inner plunger jacket 35, which traverses in contact-free manner the end wall 33 and projects into the annular space 29. Within the plunger jacket 35 is provided a shaft-like plunger core 36, which with a width-reduced projection 37 projects over the inner end of the plunger jacket 35 and with its other end can form a component of a swirling device for the outlet opening 14. The outlet channel 15 traverses the projection 37 in its end face, which is bevelled for forming a tip 38.

In the transition area to the projection 37, the plunger core 36 with the plunger jacket 35 forms a circular shoulder 39, which can engage in sealed manner on the associated, planar face of the particular pump piston 9. The projection 37 is closely adapted to the passage opening 16 and, like the latter, can be cylindrical or conical. In the starting position, the end of the projection 37 is at a limited distance from the inner face of the case body 2.

The two casing bodies 2 and 3 are only turnable relative to one another in one direction by a ratchet 40 formed by the sequence control 10. With the outer faces of their end walls 26 and 33 they in each case form a pressure handle 41 and 42 and with the outer circumference thereof form a turning handle 43 or 44. In the pump stroke end position the casing body 2 and therefore its handle 43 are substantially completely within the casing body 3. Over the outer circumference of the jacket 19 are distributed in tongue-like manner locking members 45 projecting freely and in inclined manner against the rotation direction of the casing body 2 and with which is associated on the inner circumference of the jacket 28 a tooth system 46 passing over its entire length and having a spacing corresponding to the spacing of the mounting supports 23. The tooth system 46 is formed by inwardly projecting teeth or locking members 47, which are bounded on in each case, one flank by a shallowly rising sliding face, and on the other flank by a locking shoulder 48 positioned approximately radially to the axis 21.

The locking members 45 constructed in one piece with the jacket 19 are only provided on a short portion of the casing body 2 connected in the inner end, so that in the starting position they are entirely located within the casing body 3.

In a locking position of the sequence control 10 or the ratchet 40 the projection 37 is equiaxial to a pump 6. If the casing bodies 2 and 3 are now compressed counter to the tension of a return spring 50, then the projection 37 enters the pump piston 9, perforates the closure 17 and carries with it via the shoulder 39 the pump piston 9 up to engagement on the bottom of the container 13, because the projection 37 does not project significantly over the inner end of the pump piston 9. During this pump stroke movement the content of the pump chamber 12 is completely discharged through the outlet channel 15 and the discharge nozzle.

As a result of the described construction, the plunger 11 is slightly resiliently deflectable, so that on coupling it is automatically oriented with respect to the pump piston 9. If the handles 41 and 42 are then released again, then the projection 37 is again drawn out of the container 13. Through the sawtooth-shaped construction of the piston lips the friction with respect to the container 13 is so high, that at the start of the return stroke the plunger 11 starts to be released again from the pump piston 9 and the latter remains in its end position.

In the starting position the two casing bodies 2 and 3 can be turned against one another by a switching step of the sequence control 10 and then the plunger 11 is aligned with another pump 6. During the stroke movements the rotation barrier is maintained, because the locking members 45 slide on the locking shoulders 48.

As a result of the magazine-like construction of the casing body 2, it is also possible to receive pump units with different active substances or active substance concentrations and also, following the separation of the casing bodies 2 and 3, the magazine can be reequipped with freshly filled pump units.

The return spring 50 is laterally adjacent and axially parallel to the pumps 6 in the axis 21. It is centered in the jacket 27 and is supported on the insides of the end walls 26 and 33. As a result the return spring 50 located outside the pump axes can project over one or both ends of the pumps 6. The discharge apparatus 1 can be very easily manufactured, fitted and handled and has a very compact construction. In the represented embodiment the outlet channel 15 is valve-free or open throughout, but can also be provided with an, e.g., pressure-dependent operating discharge valve.

The discharge apparatus according to FIGS. 1 to 3 can also be combined with the features of the discharge apparatus according to FIGS. 4 to 7, e.g., in such a way that the pump piston 9 can be operated in stop-limited manner over two or more successive portions of its overall stroke, so that by operating a further sequence control the next partial stroke can be performed. In FIGS. 4 to 7 corresponding parts are given the same reference numerals as in FIGS. 1 to 3, but followed by with the letter a, the descriptions applying to both embodiments.

In the discharge apparatus 1a only one pump 6a with a pump piston 8a and pump cylinder 7a is provided and located in the axis 20a. The container 13a has a much greater length than diameter, so that the pump chamber 12a can be emptied by stepwise, but return-free introduction of the pump piston 9a. For this purpose the sequence control 10a has on the inner circumference of the jacket 28a a plurality of uniformly circumferentially distributed grooves 49 in two equal groups extending in each case over half the circumference. In each case two equally long, diametrically facing grooves 49 engage two locking members 45a or longitudinal webs, which are provided on the outer circumference of the jacket 19a. Adjacent grooves 49 increase stepwise in length approximately up to the end wall 33a and pass from the open face of the casing body 3a.

Between adjacent grooves 49 is in each case provided an, e.g., toroidally projecting locking member 47a, which extends substantially over the entire length of the shorter groove and whose longitudinal edge facing the axis 20a is convexly curved or can be constructed in the manner of a rising tooth side, so that it in each case bounds the longer groove 49 laterally with a locking shoulder 48a or the associated side of said groove 49 is formed by the locking shoulder. The end portion of said groove side projecting over the adjacent shorter groove also forms a locking shoulder 48a. The end face of each groove 49 forms a stop 51 for the end of the associated locking member 45a, which can be located in the plane of the open face of the casing body 2a.

If the two casing bodies 2a and 3a are operated by compression, then the ends of the locking members 45a strike against the stops 51 of the associated grooves 49. The two casing bodies 2a and 3a can then only be rotated against one another in one direction, namely so that the locking members 45a, after resiliently jumping over the locking members 47a, pass into the vicinity of the next longer grooves 49. This can be followed by a further operation over a corresponding partial stroke, which results from the length difference between the two adjacent grooves 49.

In this embodiment the pump piston 9a is constructed in one piece with the plunger core 36 and projects over the open face of the casing body 3a. The container 13a extends approximately from the end wall 26a to the open face of the casing body 2a. From the end wall 26a the jacket 18a projects freely into the casing body 2a and closely surrounds the container 13a as a mounting support 23a on the outer circumference. The casing body 2a is longer than the casing body 3a, so that the handle 43a, even in the end position, still projects in accessible manner over the body 3a.

We claim:

1. A unit-dose dispenser for manual discharge of a single dose of a flowable substance in the form of a spray, comprising a casing which has a nozzle and at least one shoulder on a side of this nozzle, the nozzle having a piston member extending inwardly from an outlet opening, the piston member having at least one discharge channel, a container of the substance to be discharged being operatively positioned with respect to the piston member, and a seal being arranged across the container to seal in all the substance to be discharged, the piston member having a piercing member which extends towards the seal, whereby on pressing the container onto the piston member the seal is pierced to allow the contents of the container to be expelled along the discharge channel and out through the outlet opening in the form of the spray.

2. A dispenser according to claim 1, wherein the seal is formed by a stopper which is moveably engaged inside the container and has a central membrane which, in use, is pierced by the piercing member.

3. A dispenser according to claim 2, wherein the piercing member is at least partly hollow, thereby forming the discharge channel of the piston.

4. A dispenser according to claim 3, wherein the piercing member extends along the axis of the piston member to the outlet opening.

5. A dispenser according to claim 1 further comprising shoulders on either side of the nozzle.

6. A dispenser according to claim 1, wherein the container is contained in a casing body which engages on the inside of the casing, the casing body having a bead cooperating with a bead on the inside of the casing to form a snap connection.

7. A dispenser according to claim 1, wherein the container contains a pharmaceutical substance.

8. A dispenser according to claim 1, wherein the container is contained in a casing body which is positioned inside the casing.

9. A dispenser according to claim 1, wherein the container is contained in a casing body and the casing body is positioned inside the casing and the casing and the casing body are provided with a locking member each, the casing and the casing body being moveable relative to each other after the locking member on the casing has been moved past the locking member of the casing body.

10. A dispenser according to claim 1, wherein the container is contained in a casing body providing a pressure handle at its bottom.

11. A dispenser according to claim 10, wherein the casing body comprises at least one rib on which the container is supported in spaced relationship to the bottom.

12. A dispenser according to claim 1, wherein the piercing member is inserted into an inner plunger jacket of the casing.

13. A dispenser according to claim 12, wherein the plunger jacket has a shoulder which is designed to sealingly engage the seal of the container.

14. A dispenser according to claim 2, wherein the seal has, adjacent to its central membrane, an equiaxial recess, proximate the piercing member.

* * * * *